(12) United States Patent
Kai et al.

(10) Patent No.: US 8,012,606 B2
(45) Date of Patent: *Sep. 6, 2011

(54) HETEROCYCLIC COMPOUND AND ORGANIC ELECTROLUMINESCENT DEVICE USING THE SAME

(75) Inventors: Takahiro Kai, Kitakyushu (JP);
Toshihiro Yamamoto, Kitakyushu (JP);
Masaki Komori, Kitakyushu (JP);
Masanori Hotta, Kitakyushu (JP);
Yuichi Sawada, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 607 days.

This patent is subject to a terminal disclaimer.

(21) Appl. No.: 11/989,779

(22) PCT Filed: Jul. 27, 2006

(86) PCT No.: PCT/JP2006/314849
§ 371 (c)(1),
(2), (4) Date: Jan. 31, 2008

(87) PCT Pub. No.: WO2007/015412
PCT Pub. Date: Feb. 8, 2007

(65) Prior Publication Data
US 2009/0153031 A1     Jun. 18, 2009

(30) Foreign Application Priority Data
Aug. 3, 2005 (JP) ................... 2005-225080

(51) Int. Cl.
H01L 51/50 (2006.01)
C07D 319/24 (2006.01)
C07D 339/08 (2006.01)
H01J 1/62 (2006.01)

(52) U.S. Cl. ........ 428/690; 428/917; 313/504; 313/506; 549/17; 549/359

(58) Field of Classification Search .................. None
See application file for complete search history.

(56) References Cited

U.S. PATENT DOCUMENTS

| | | | |
|---|---|---|---|
| 7,605,277 B2 * | 10/2009 | Kai et al. ........... | 549/359 |
| 2002/0034655 A1 | 3/2002 | Watanabe et al. | |
| 2002/0096995 A1 * | 7/2002 | Mishima et al. ........ | 313/506 |
| 2005/0014018 A1 | 1/2005 | Klubek et al. | |

FOREIGN PATENT DOCUMENTS

| | | | |
|---|---|---|---|
| DE | 19733882 A1 * | 2/1999 | |
| JP | 2001-313178 A | 11/2001 | |
| JP | 2004-146110 A | 5/2004 | |
| WO | WO-2005/075451 A1 | 8/2005 | |
| WO | WO-2006/041263 A1 | 4/2006 | |
| WO | WO-2006/096399 A2 | 9/2006 | |

OTHER PUBLICATIONS

Wang et al., Dyes and Pigments, vol. 54, (2002), p. 265-274.*
Niume et al., Journal of Polymer Science: Poymer Chemistry Edition, vol. 17, pp. 2371-2385 (1979).*
Subramaniam et al., Journal of Polymer Science: Part A: Polymer Chemistry, vol. 26, pp. 1553-1560 (1988).*
European Patent Office machine translation of Description of DE 19733882, which was published Feb. 1999.*
Clarke et al., "Heterocyclic free radicals. VI. Substituent effects on the distribution," Journal of the Chemical Society, Perkin Translations 2: Physical Organic Chemistry, 1976, vol. 1, pp. 114-124.
Okamoto et al., "Remarkable Structure Deformation in Phenothiazine Trimer Radical Cation," Organic Letters, 2004, vol. 6, No. 20, pp. 3493-3496.
Hoerhold et al., "A novel approach to light emitting polyarylenes: cyclization of poly(arylene vinylenes)," Synthetic Metals, 1995, vol. 69, No. 1-3, pp. 525-528.

* cited by examiner

Primary Examiner — Dawn L. Garrett
(74) Attorney, Agent, or Firm — Birch, Stewart, Kolasch & Birch, LLP

(57) ABSTRACT

Disclosed is an organic electroluminescent device (organic EL device) which is improved in luminous efficiency, fully secured of driving stability, and simple in structure and also disclosed is a heterocyclic compound useful for the said device. Specifically, the heterocyclic compound is represented by the following general formula (I) and the organic EL device comprises an organic layer containing the said heterocyclic compound. In general formula (I), $X_1$ and $X_2$ respectively denote O, S, or N—R, R denotes a hydrogen atom, an alkyl group, or a substituted or unsubstituted aryl group, $Ar_1$, $Ar_2$, $Ar_3$, and $Ar_4$ respectively denote a substituted or unsubstituted aryl group, $Ar_1$, $Ar_2$, and the nitrogen atom bonded thereto or $Ar_3$, $Ar_4$, and the nitrogen atom bonded thereto may form a nitrogen-containing hetero ring, and m and n respectively denote an integer of 1 or 2.

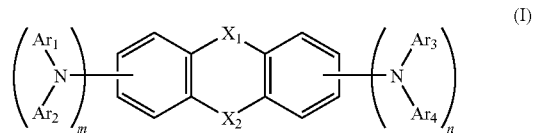

10 Claims, 1 Drawing Sheet

Fig 1

HETEROCYCLIC COMPOUND AND ORGANIC ELECTROLUMINESCENT DEVICE USING THE SAME

FIELD OF TECHNOLOGY

This invention relates to a condensed heterocyclic compound having a substituted amino group and to an organic electroluminescent device using the same.

BACKGROUND TECHNOLOGY

In the development of an electroluminescent device utilizing an organic material (hereinafter referred to as an organic EL device), a device developed by optimizing the kind of electrodes and disposing a hole-transporting layer comprising an aromatic amine and a light-emitting layer comprising 8-hydroxyquinoline aluminum complex as thin films between the electrodes for the purpose of improving the efficiency of injecting electrical charges from the electrodes has brought about a noticeable improvement in luminous efficiency over the conventional devices utilizing single crystals of anthracene and the like. Since then, the developmental works of organic electroluminescent devices have been focused on their commercial applications to high-performance flat panels characterized by self luminescence and high-speed response.

The aforementioned device comprising an aromatic diamine in the hole-transporting layer and 8-hydroxyquinoline aluminum complex in the light-emitting layer and many others utilize fluorescence. However, utilization of phosphorescence, that is, emission of light from the triplet excited state, is expected to raise the luminous efficiency three to four times that of the conventional devices utilizing fluorescence (singlet). For this reason, a large number of developmental works are directed to phosphorescent dopants.

Patent document 1: JP2003-515897 A
Patent document 2: JP2001-313178 A
Patent document 3: JP2002-352957 A
Non-patent document 1: Nature, Vol. 395, p. 151, 1998
Non-patent document 2: Appl. Phys. Lett., Vol. 75, p. 4, 1999

The non-patent document 1 reports that the use of a platinum complex (PtOEP) enables the device to emit red light at high efficiency. Thereafter, the non-patent document 2 reports that the efficiency of emission of green light improves appreciably by doping the light-emitting layer with an iridium complex or tris(2-phenylpyridine)iridium [Ir(ppy)3]. This document further reports that optimization of the light-emitting layer enables this iridium complex to show extremely high luminous efficiency even when the structure of the device is simplified still further.

In applications of organic EL devices to display devices such as flat panel displays, it is necessary to improve the luminous efficiency of the device and, at the same time, to fully secure the driving stability of the device. However, the organic electroluminescent device described in the non-patent document 2, that is, a device which utilizes a phosphorescent molecule and shows a high luminous efficiency, lacks sufficient driving stability for practical use at the present time.

In the non-patent document 2, 4,4'-bis(9-carbazolyl)biphenyl (CBP) or 3-phenyl-4-(1'-naphthyl)-5-phenyl-1,2,4-triazole (TAZ) is used in the light-emitting layer and a phenanthroline derivative is used in the hole-blocking layer. Moreover, CBP is described as a preferable host material in the non-patent documents 1 and 2.

However, as the aforementioned CBP has a property of facilitating the flow of holes and obstructing the flow of electrons, the use of CBP destroys the balance of electrical charges in the light-emitting layer and allows excess holes to flow out to the side of electron-transporting layer and, as a result, the luminous efficiency of Ir(ppy)3 drops. On the other hand, TAZ has a property of facilitating the flow of electrons and obstructing the flow of holes and the use of TAZ shifts the light-emitting range to the side of the hole-transporting layer. In this case, the hole-transporting material in use affects the luminous efficiency of Ir(ppy)3. For example, the use of 4,4'-bis[N-(1-naphthyl)-N-phenylamino]biphenyl (NPB) which is most often used in the hole-transporting layer for its high performance, high reliability, and long service life causes transition of energy to occur from Ir(ppy)3 to NPB and the luminous efficiency drops.

As a means to solve the aforementioned problem, the use of 4,4'-bis[N,N'-(3-toluoyl)amino]-3,3'-dimethylbiphenyl (HMTPD) to which transition of energy from Ir(ppy)3 does not occur is conceivable, but this compound is not considered sufficiently durable.

Furthermore, CBP and TAZ readily undergo crystallization and cohesion thereby deteriorating the shape of their thin films and, besides, it is difficult to merely observe the Tg because of their high crystallinity. The instability of the shape of thin film inside the light-emitting layer adversely affects the device by shortening the driving life and lowering the heat resistance. For the aforementioned reasons, the largest problem facing the organic electroluminescent devices utilizing phosphorescence is how to secure the driving stability of the device.

DISCLOSURE OF THE INVENTION

Problems to be Solved by the Invention

In applications of organic EL devices to display devices such as flat panel devices, it is necessary to improve the luminous efficiency of the device and, at the same time, to fully secure the driving stability of the device. Under the aforementioned circumstances, an object of this invention is to provide an organic EL device which performs at high efficiency with good driving stability and a compound suitable for the said device.

Means to Solve the Problems

The inventors of this invention have found that a heterocyclic compound represented by the following general formula (I) has an excellent ability to transport electrical charges (electrons and holes) and high triplet excitation energy. They have additionally found that the said compound shows good stability when formed into thin film and good heat stability and completed this invention.

This invention relates to a heterocyclic compound represented by the following general formula (I)

wherein $X_1$ and $X_2$ independently denote O, S, or N—R, R denotes a hydrogen atom, a substituted or unsubstituted alkyl group, or a substituted or unsubstituted aryl group, $Ar_1$, $Ar_2$, $Ar_3$, and $Ar_4$ denote independently a substituted or unsubstituted aryl group, $Ar_1$, $Ar_2$, and the nitrogen atom bonded thereto or $Ar_3$, $Ar_4$, and the nitrogen atom bonded thereto may form a nitrogen-containing hetero ring, and m and n are independently 1 or 2.

Preferable examples of the heterocyclic compounds represented by the general formula (I) are shown below.

In general formulas (II), (III), and (IV), $Ar_1$, $Ar_2$, $Ar_3$, $Ar_4$, m, n, and R are as defined in the aforementioned general formula (I).

In general formulas (I) to (IV), the groups $Ar_1$, $Ar_2$, $Ar_3$, and $Ar_4$ are preferably phenyl, naphthyl, phenanthryl, pyridinyl, pyrazyl, pyrimidyl, imidazoly, thienyl, or furyl, either unsubstituted or substituted with a lower alkyl group, a lower alkoxy group, an aryl group of 4 to 10 carbon atoms, or an aryloxy group of 4 to 10 carbon atoms. The groups $Ar_1$, $Ar_2$, $Ar_3$, and $Ar_4$ may be identical with or different from one another.

In the case where $Ar_1$, $Ar_2$, and the nitrogen atom bonded thereto or $Ar_3$, $Ar_4$, and the nitrogen atom bonded thereto form a nitrogen-containing hetero ring, preferable examples of such hetero rings are N-carbazolyl, N-phenoxazinyl, N-phenothiazinyl, and N—carbolinyl groups, either unsubstituted or substituted with a lower alkyl group, a lower alkoxy group, an aryl group of 4 to 10 carbon atoms, or an aryloxy group of 4 to 10 carbon atoms. The groups —$NAr_1Ar_2$ and —$NAr_3Ar_4$ may be identical with or different from each other.

Further, this invention relates to an organic electroluminescent device that has an organic layer comprising the aforementioned heterocyclic compound. A preferable example of this organic layer is a light-emitting layer, a hole-transporting layer, or a hole-injecting layer. Another preferable example of this organic layer is a light-emitting layer containing a phosphorescent dopant or a hole-transporting layer in contact with the phosphorescent light-emitting layer.

In general formulas (I) to (IV), the unsubstituted aryl groups denote carbocyclic aromatic groups such as phenyl, naphthyl, anthryl, and phenanthryl and heterocyclic aromatic groups such as furyl, thienyl, and pyridyl. Preferably, they are carbocyclic aromatic groups of 6 to 18 carbon atoms and heterocyclic aromatic groups of 4 to 17 carbon atoms and 1 to 4 hetero atoms. More preferably, they are carbocyclic aromatic groups of 6 to 16 carbon atoms and heterocyclic aromatic groups of 4 to 14 carbon atoms. The aryl group may have 1 to 4 rings, preferably 1 to 3 rings, and these rings may be condensed or uncondensed. In the case where the unsubstituted aryl group in question is used in the light-emitting layer containing a phosphorescent dopant or in the hole-transporting layer in contact with the phosphorescent light-emitting layer, $Ar_1$, $Ar_2$, $Ar_3$, and $Ar_4$ are preferably uncondensed aryl groups of 1 to 3 rings.

Preferable examples of the substituted aryl groups are carbocyclic aromatic groups of 6 to 16 carbon atoms or heterocyclic aromatic groups of 4 to 14 carbon atoms substituted with an alkyl group, an alkoxy group, an aryl group of 4 to 12 carbon atoms, or an aryloxy group of 4 to 12 carbon atoms. In the case where the substituted aryl groups are heterocyclic aromatic groups, the hetero atom may be N, S, or O and the total number of hetero atoms is preferably in the range of 1 to 4. Moreover, $Ar_1$, $Ar_2$, and the nitrogen atom bonded thereto or $Ar_3$, $Ar_4$, and the nitrogen atom bonded thereto may form a nitrogen-containing hetero ring. In this case, the groups —$NAr_1Ar_2$ and —$NAr_3Ar_4$ represent substituted or unsubstituted N-carbazolyl, N-phenoxazinyl, N-phenothiazinyl, and N-carbolinyl groups.

Concrete examples of the unsubstituted aryl groups are phenyl, naphthyl, phenanthryl, indenyl, azulenyl, heptalenyl, acenaphthylenyl, phenalenyl, fluorenyl, anthryl, biphenylenyl, triphenylenyl, tetraphenylenyl, pyrenyl, chrysenyl, picenyl, perylenyl, pentaphenyl, pentacenyl, hexaphenyl, hexacenyl, rubicenyl, coronenyl, trinaphthylenyl, heptaphenyl, heptacenyl, pyranthrenyl, ovalenyl, furyl, thienyl, pyridyl, carbazolyl, thianthrenyl, pyranyl, isobenzofuranyl, chromenyl, xanthenyl, phenoxathinyl, pyrrolyl, imidazolyl, pyrazolyl, isothiazolyl, isoxazolyl, pyrazinyl, pyrimidinyl, pyridazinyl, indolidinyl, isoindolyl, purinyl, indolyl, quinolyl, isoquinolyl, acridinyl, phenanthrolinyl, phthalazinyl, naphthyridinyl, quinoxalinyl, quinazolinyl, phenanthridinyl, perimidinyl, phenanthrolinyl, phenazinyl, and furazanyl. Of the groups listed above, preferable are phenyl, naphthyl, phenanthryl, indenyl, fluorenyl, anthryl, pyrenyl, perylenyl, pentaphenyl, coronenyl, furyl, thienyl, pyriyl, carbazolyl, pyranyl, pyrrolyl, imidazolyl, pyrazolyl, isothiazolyl, isoxazolyl, pyrimidinyl, indolidinyl, indolyl, quinolyl, isoquinolyl, acridinyl, phenanthrolinyl, qinoxalinyl, quinazolinyl, and phenazinyl.

The unsubstituted alkyl groups are preferably alkyl groups of 1 to 6 carbon atoms. Concrete examples are methyl, ethyl, propyl, isopropyl, butyl, sec-butyl, tert-butyl, pentyl, hexyl, heptyl, octyl, and stearyl.

The substituents in the substituted aryl groups and substituted alkyl groups include nitro, cyano, alkyl, aralkyl, aralkyloxy, alkoxy, aryl, and aryloxy groups. Concretely, the alkyl groups include methyl, ethyl, propyl, isopropyl, butyl, sec-butyl, tert-butyl, pentyl, hexyl, heptyl, octyl, and stearyl. The aralkyl groups include 2-phenylisopropyl, benzyl, and triphenylmethyl. The alkoxy groups include methoxy, ethoxy, propoxy, n-butoxy, sec-butoxy, tert-butoxy, pentyloxy, hexyloxy, n-octyloxy, tert-octyloxy, and stearyloxy. The aralkyloxy groups include benzyloxy. The aryl groups include phenyl, biphenylyl, naphthyl, phenanthryl, indenyl, naphthyl, azulenyl, heptalenyl, acenaphthylenyl, phenalenyl, fluorenyl, anthryl, biphenylenyl, triphenylenyl, tetraphenylenyl, pyrenyl, chrysenyl, picenyl, perylenyl, pentaphenyl, pentacenyl, hexaphenyl, hexacenyl, rubicenyl, coronenyl, trinaphthylenyl, heptaphenyl, heptacenyl, pyranthrenyl, ovalenyl, furyl, thienyl, pyridyl, carbazolyl, thianthrenyl, pyranyl, isobenzofuranyl, chromenyl, xanthenyl, phenoxathinyl, pyrrolyl, imidazolyl, pyrazolyl, isothiazolyl, isoxazolyl, pyrazinyl, pyrimidinyl, pyridazinyl, indolidinyl, isoindolyl, purinyl, indolyl, quinolyl, isoquinolyl, acridinyl, phenanthrolinyl, phthalizinyl, naphthyridinyl, qinoxalinyl, quinazolinyl, phenanthridinyl, perimidinyl, phenanthrolinyl, phenazinyl, furazanyl, 4-methylbiphenylyl, 3-nitrophenyl, 4-cyanophenyl, methoxyphenyl (o-, m-, and p-), tolyl (o-, m-, and p-), cumenyl (o-, m-, and p-), mesityl, 4-phenoxyphenyl, and 5-methylnaphthyl. The aryloxy groups include those aryloxy groups which are derived from the aforementioned aryl groups. The substituents listed above may link to the adjacent substituents to form new saturated rings or aromatic rings.

Representative examples of the heterocyclic compounds of this invention are shown in Tables 1 to 4 below, but this invention is not limited to these examples.

TABLE 1

1

2

3

TABLE 1-continued

4

5

6

TABLE 1-continued

7

8

TABLE 2

9

10

TABLE 2-continued

11

12

13

14

TABLE 2-continued

15

16

TABLE 3

17

18

19

TABLE 3-continued

20

21

22

TABLE 3-continued

23

24

TABLE 4

25

26

TABLE 4-continued

27

28

29

30

31

TABLE 4-continued

32

One of the methods applicable to the synthesis of the heterocyclic compounds represented by general formula (I) of this invention is based on the reaction of an amine with an aryl halide, both corresponding to the target heterocyclic compound, in an organic solvent or without a solvent in the presence of a base and a catalyst in an atmosphere of nitrogen at a temperature in the range of 100 to 200° C. for a period of 1 to 50 hours. The halogen atom in the aryl halide may be chlorine, bromine, or iodine. The base is selected from inorganic bases such as potassium carbonate, sodium carbonate, lithium hydroxide, sodium hydroxide, sodium tert-butoxide, and potassium tert-butoxide or from organic bases such as pyridine, picoline, and triethylamine. The catalysts useful for the reaction include copper-based catalysts such as copper powder, copper oxide, copper halides, and copper sulfate and palladium complex-based catalysts formed from a palladium source such as palladium acetate and bis(dibenzylideneacetone)palladium and a ligand such as tri-tert-butylphosphine. The solvent may be any compound which dissolves the raw material and lets the reaction to proceed; for example, toluene, xylene, tetralin, quinoline, nitrobenzene, dimethyl sulfoxide, and N,N-dimethylformamide.

Upon completion of the reaction, the organic layer is separated by addition of water, concentrated, washed with a low-boiling solvent such as ethyl acetate, and dried under reduced pressure to give a heterocyclic compound useful for this invention. In the case where this compound is used as an organic EL material, it is preferably purified further by sublimation.

The organic EL device of this invention is explained below.

The organic EL device of this invention can be fabricated in a variety of structures, but it is basically constituted of an organic layer containing the aforementioned heterocyclic compound sandwiched between a pair of electrodes (cathode and anode). The heterocyclic compound can be used alone in the hole-injecting layer, hole-transporting layer, light-emitting layer, hole-blocking layer, electron-injecting layer, or electron-transporting layer and, as needed, a hole-injecting material, hole-transporting material, hole-blocking material, light-emitting material, electron-injecting material, or electron-transporting material may be added to the layer containing the heterocyclic compound. Particularly, in the case where the heterocyclic compound is used in the light-emitting layer, the addition of another light-emitting material to this light-emitting layer makes it possible to emit light of different wavelength or to improve the luminous efficiency. It is further possible to laminate a layer of hole-injecting material, hole-transporting material, light-emitting material, hole-blocking material, electron-injecting material or electron-transporting material to the layer of the heterocyclic compound to form a hole-injecting layer, hole-transporting layer, light-emitting layer, hole-blocking layer, electron-injecting layer, or electron-transporting layer.

Concrete examples of the layered structures are listed below.

1 anode/organic light-emitting layer/cathode 2 anode/hole-transporting layer/organic light-emitting layer/cathode 3 anode/hole-transporting layer/organic light-emitting layer/hole-blocking layer/cathode 4 anode/hole-injecting layer/hole-transporting layer/organic light-emitting layer/cathode 5 anode/hole-injecting layer/hole-transporting layer/organic light-emitting layer/hole-blocking layer/cathode 6 anode/organic light-emitting layer/electron-transporting layer/cathode 7 anode/organic light-emitting layer/electron-transporting layer/electron-injecting layer/cathode 8 anode/organic light-emitting layer/hole-blocking layer/electron-transporting layer/electron-injecting layer/cathode 9 anode/hole-transporting layer/organic light-emitting layer/hole-blocking layer/electron-transporting layer/cathode 10 anode/hole-injecting layer/hole-transporting layer/organic light-emitting layer/electron-transporting layer/cathode 11 anode/hole-injecting layer/hole-transporting layer/organic light-emitting layer/electron-transporting layer/hole-blocking layer/cathode 12 anode/hole-injecting layer/hole-transporting layer/organic light-emitting layer/electron-transporting layer/electron-injecting layer/cathode

13 anode/hole-injecting layer/hole-transporting layer/organic light-emitting layer/hole-blocking layer/electron-transporting layer/electron-injecting layer/cathode

In the aforementioned structures, the hole-injecting layer, the electron-injecting layer, and the hole-blocking layer are not always necessary, but providing these layers improves the luminous efficiency.

The heterocyclic compound of this invention is suitable for use in a light-emitting layer, particularly for use in a light-emitting layer containing a phosphorescent dopant. In such a case, the light-emitting layer contains the heterocyclic compound preferably as the main component and desirably as a host material doped with a phosphorescent dopant.

The phosphorescent dopants include organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used.

Preferable phosphorescent dopants include complexes containing a noble metal element such as Ir as the central metal, a typical example being Ir(ppy)3, complexes such as Ir(bt)2• acac3, and complexes such as PtOEt3. Concrete examples of these complexes are shown below, but the preferable phosphorescent dopants are not limited to these examples.

In the case where the light-emitting layer contains a phosphorescent dopant, the content of the dopant is preferably in the range of 1 to 10 wt %.

| Explanation of the Symbols | |
|---|---|
| 1 | Substrate |
| 2 | Anode |
| 3 | Hole-injecting layer |
| 4 | Hole-transporting layer |
| 5 | Light-emitting layer |
| 6 | Electron-transporting layer |
| 7 | Cathode |

PREFERRED EMBODIMENTS OF THE INVENTION

Figure 1:
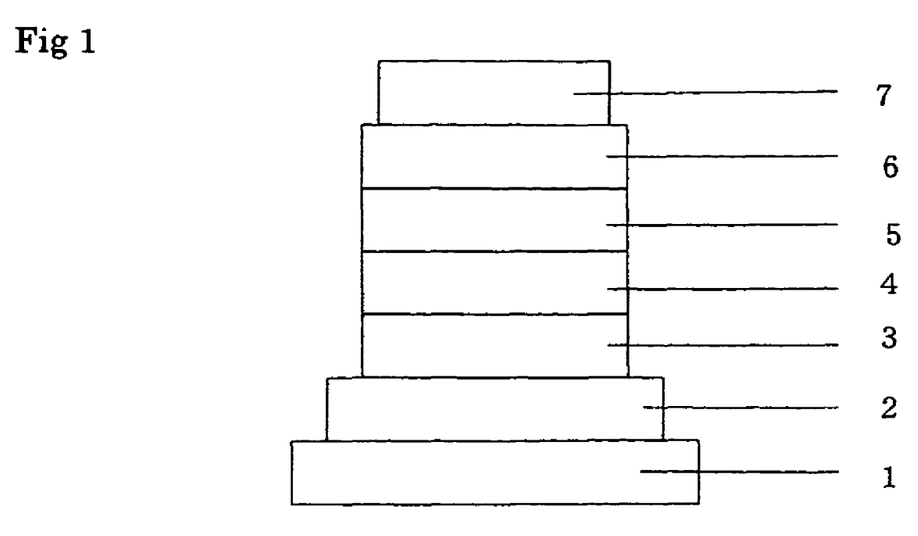
FIG. 1 illustrates the schematic cross section of an example of the organic EL device.

The structure of the organic EL device of this invention is described below with reference to the drawing, but the structure is not limited at all to the one illustrated in the FIGURE.

FIG. 1 illustrates schematically the cross section of a common organic EL device and the symbols respectively denote the following; 1 substrate, 2 anode, 3 hole-injecting layer, 4 hole-transporting layer, 5 light-emitting layer, 6 electron-transporting layer, and 7 cathode. It is preferable that the organic EL device comprises the substrate, anode, hole-transporting layer, light-emitting layer, electron-transporting layer, and cathode as essential layers. In this case, the hole-injecting layer 3 may be omitted and another layer such as a hole-blocking layer may be added if necessary.

The structure shown in FIG. 1 may be reversed, that is, it is possible to stack the cathode 7, electron-transporting layer 6, light-emitting layer 5, hole-transporting layer 4, and anode 2 in this order on the substrate 1 and it is also possible to provide the organic EL device of this invention between two substrates at least one of which is highly transparent.

The organic EL device of this invention is applicable to a single device, a device with its structure arranged in array, and device in which the anode and the cathode are arranged in X-Y matrix.

EXAMPLES

This invention is described in more detail below with reference to the accompanying examples, but is not limited to these examples. Compound 1, Compound 3, Compound 8, Compound 9, Compound 12, and Compound 27 were synthesized respectively in accordance with the synthetic routes shown below. The compound number corresponds to the one in Tables 1 to 4.

25

1

8

9

26

3

27

Synthetic Example 1

Synthesis of 2,7-dinitrodibenzodioxin

To 1600 ml of acetic acid was added 60 g (0.326 mole) of dibenzodioxin and 280 ml of fuming nitric acid was added in drops to the mixture over a period of 1 hour with stirring at room temperature. After completion of the dropwise addition, the mixture was stirred further for 2 hours and a precipitate was recovered by filtration. The precipitate was reslurried with methanol and dried under reduced pressure to give 85.7 g (0.313 mole, 96.0% yield) of 2,7-dinitrodibenzodioxin. The product thus obtained showed a purity of 96.5 area % (HPLC, 254 nm).

Synthetic Example 2

Synthesis of 2,7-diaminodibenzodioxin

To a mixture of 1200 ml of anisole and 800 ml of THF were added 69.7 g (0.254 mole) of 2,7-dinitrodibenzodioxin and 22.2 g of 10% palladium/carbon and hydrogen gas was passed through the mixture with stirring at room temperature for 8 hours. The 10% palladium/carbon was removed by filtration, then a precipitate containing the 10% palladium/carbon was collected by filtration, and the precipitate was rinsed with THF. The rinsings were concentrated and dried under reduced pressure to give 25.0 g (0.117 mole, 46.0% yield) of 2,7-diaminodibenzodioxin. The product showed a purity of 98.1% (HPLC, 254 nm).

Synthetic Example 3

Synthesis of 2,7-bis(acetylamino)dibenzodioxin

To a mixture of 900 ml of toluene and 900 ml of THF were added 50.0 g (0.233 mole) of 2,7-diaminodibenzodioxin and 55.3 g (0.699 mole) of pyridine and to the resulting mixture was added 59.5 g (0.583 mole) of acetic anhydride in drops over a period of 10 minutes at room temperature with stirring. After the dropwise addition, the mixture was stirred overnight and a precipitate was recovered by filtration. The precipitate was reslurried with toluene (250 mix 2) and dried under reduced pressure to give 57.0 g (0.191 mole, 82.0% yield) of 2,7-bis(acetylamino)dibenzodioxin. The product showed a purity of 99.3 area % (HPLC, 254 nm).

Synthetic Example 4

Synthesis of 2,7-bis(N-phenylacetylamino)dibenzodioxin

A slurry prepared from 34.3 g (0.115 mole) of 2,7-bis(acetylamino)dibenzodioxin, 96.4 g (0.576 mole) of iodobenzene, 48.2 g (0.253 mole) of copper (I) iodide, 63.6 g (0.460 mole) of potassium carbonate, and 1500 ml of quinoline was heated with stirring at 170° C. for 48 hours. The reaction mixture was cooled to room temperature, 500 ml of methylene chloride and 500 ml of water were added, and a precipitate was separated by filtration. To the filtrate was added 500 ml of water and the organic layer was separated from the aqueous layer. The organic layer was concentrated and dried under reduced pressure to give 79.4 g of a crude product which was used without purification in the next reaction.

Synthetic Example 5

Synthesis of 2,7-bis(phenylamino)dibenzodioxin

To a mixture of 500 g of methanol and 100 g of a 24% aqueous solution of sodium hydroxide was added 79.4 g of the diacetamide compound obtained in Synthetic Example 4 and the mixture was heated under reflux for 20 hours. The reaction mixture was cooled to room temperature, 1000 ml of water was added, and a precipitate was recovered by filtration. The precipitate was rinsed with water and dried under reduced pressure to give 44.3 g of 2,7-bis(phenylamino)dibenzodioxin. The crude product thus obtained was purified by reslurrying under heat with methanol. The yield was 31.8 g [0.087 mole, 75.7% (2 steps)] and the purity was 98.4 area % (HPLC, 254 nm).

Synthetic Example 6

Synthesis of 2,7-bis(N-3-pyridylacetylamino)dibenzodioxin

A slurry prepared from 7.0 g (0.023 mole) of 2,7-bis(acetylamino)dibenzodioxin, 12.0 g (0.059 mole) of 3-iodopyridine, 9.8 g (0.051 mole) of copper (I) iodide, 12.9 g (0.093 mole) of potassium carbonate, and 230 ml of quinoline was heated with stirring at 170° C. for 48 hours. The reaction mixture was cooled to room temperature, 100 ml of methylene chloride and 100 ml of water were added, and a precipitate was separated by filtration. To the filtrate was added 100 ml of water and the organic layer was separated from the aqueous layer. The organic layer was concentrated and dried under reduced pressure to give 23.5 g of a crude product which was used without purification in the next reaction.

Synthetic Example 7

Synthesis of 2,7-bis(3-pyridylamino)dibenzodioxin

To a mixture of 75 g of methanol and 35.6 g of a 24% aqueous solution of sodium hydroxide was added 23.5 g of the diacetamide compound obtained in Synthetic Example 6 and the mixture was heated under reflux for 120 hours. The reaction mixture was cooled to room temperature, 200 ml of water was added, and a precipitate was recovered by filtration. The precipitate was rinsed with water and dried under reduced pressure to give 8.51 g of 2,7-bis(3-pyridylamino)dibenzodioxin. The crude product thus obtained was purified by reslurrying under heat with THF and by reslurrying under heat with methanol. The yield was 8.39 g [0.023 mole, 97.3% (2 steps)] and the purity was 95.7 area % (HPLC, 254 nm).

Synthetic Example 8

Synthesis of 2,7-diacetylthianthrene

A mixture of 34.3 g (0.158 mole) of thianthrene, 86.0 g (0.645 mole) of aluminum chloride, and 160 ml of dichloromethane was cooled below 10° C. and, at this temperature, 90 ml (1.27 mole) of acetyl chloride was added in drops over a period of 1 hour. After the dropwise addition, the temperature was returned to room temperature and the mixture was stirred overnight. The reaction mixture was poured slowly into cold water and a yellow precipitate was collected by filtration. The methylene chloride layer in the filtered mother liquor was concentrated and a yellowish brown precipitate was collected by filtration. Acetone was added to these precipitates, the matters insoluble in acetone were filtered off and the filtered mother liquor was concentrated to give a crude product. The crude product was recrystallized from toluene to give 2,7-diacetylthianthrene. The yield was 24.6 g (0.082 mole, 52% yield) and the purity was 95.6 area % (HPLC, 254 nm).

Synthetic Example 9

Synthesis of 2,7-bis(1-hydroxyiminoethyl)thianthrene

To a solution of 11.3 g (0.034 mole) of 2,7-diacetylthianthrene in 550 ml of ethanol was added 30 ml of a 50% aqeuous solution of hydroxylamine and the mixture was heated at 80° C. for 7 hours with stirring. The reaction mixture was cooled to room temperature, then poured into 3 L of water, and acidified with hydrochloric acid to a pH of 3 to 4. The reaction mixture was extracted with ethyl acetate and the organic layer was concentrated to give 11.86 g of a crude product. Ethyl acetate was added to the crude product and the insoluble substance or 2,7-bis(1-hydroxyiminoethyl)thianthrene was collected by filtration. The yield was 5.93 g (0.018 mole, 53% yield) and the purity was 96.0 area % (HPLC, 254 nm).

Synthetic Example 10

Synthesis of 2,7-bis(acetylamino)thianthrene

To 264 g of polyphosphoric acid was added 15.1 g (0.0455 mole) of 2,7-bis(1-hydroxyiminoethyl)thianthrene and the mixture was heated at 110° C. for 40 minutes with stirring. The reaction mixture was cooled to room temperature and then poured into 5 L of stirred water. A precipitate was collected by filtration, dissolved in 500 ml of methanol, and the insoluble matters were separated by filtration. The filtered mother liquor was poured into 5 L of water and the insoluble product or 2,7-bis(acetylamino)thianthrene was collected by filtration. The yield was 9.23 g (0.028 mole, 61% yield) and the purity was 80 area % (HPLC, 254 nm).

Synthetic Example 11

Synthesis of 2,7-diaminothianthrene

A mixture of 5.75 g (0.0174 mole) of 2,7-bis(acetylamino) thianthrene, 12 ml of concentrated hydrochloric acid, and 140 ml of ethanol was heated under reflux for 6 hours. The reaction mixture was cooled to room temperature and a precipitate was collected by filtration. The precipitate was added to a mixture of 13.5 ml of concentrated hydrochloric acid and 355 ml of water and the insoluble matters were separated by filtration. The filtered mother liquor was poured into an aqueous solution of sodium hydroxide and the precipitate or 2,7-diaminothianthrene was collected by filtration. The yield was 3.7 g (0.0158 mole, 91% yield) and the purity was 88.2 area % (HPLC, 254 nm).

Example 1

Synthesis of 2,7-bis(9-carbazolyl)dibenzodioxin (Compound 12)

To a solution of 0.79 g (3.5 millimoles) of palladium (II) acetate in 50 ml of xylene was added 2.84 g (11.2 millimoles) of tri-tert-butylphosphine and the mixture was heated at 80° C. for 30 minutes with stirring. This solution was transferred into a solution heated at 80° C. of 7.54 g (0.0352 mole) of 2,7-diaminodibenzodioxin, 22.0 g (0.0705 mole) of 2,2'-dibromobiphenyl, and 28.41 g (0.296 mole) of sodium tert-butoxide in 500 ml of xylene. The mixture was then heated up to 125° C. and heated at this temperature with stirring for 5 hours. The reaction mixture was cooled to room temperature and 250 ml of water was added. The organic layer was separated from the aqueous layer, the aqueous layer was washed with 250 ml of toluene, and the organic layers were combined, concentrated, and dried under reduced pressure to give 14.8 g of a crude product. The crude product was subjected to reslurrying under heat with ethyl acetate and dried under reduced pressure to give 4.60 g (0.00894 mole, 25.4% yield) of 2,7-bis(9-carbazolyl)dibenzodioxin. The product showed a purity of 99.2 area % (HPLC, 254 nm). The product was purified further by sublimation; FD-MS, m/z 514 [M]$^+$, m.p. 348° C., glass transition temperature (Tg) 118° C.

Example 2

Synthesis of 2,7-bis(N-3-biphenylyl-N-phenylamino)dibenzodioxin (Compound 1)

To a solution of 0.28 g (1.24 millimoles) of palladium (II) acetate in 20 ml of xylene was added 0.96 g (4.28 millimoles) of tri-tert-butylphosphine and the mixture was heated at 80° C. for 30 minutes with stirring. This solution was transferred into a solution heated at 80° C. of 9.0 g (0.025 mole) of 2,7-bis(phenylamino)dibenzodioxin, 14.3 g (0.061 mole) of 3-bromobiphenyl, and 9.53 g (0.099 mole) of sodium tert-butoxide in 200 ml of xylene. The mixture was then heated up to 140° C. and heated at this temperature with stirring for 6 hours. The reaction mixture was cooled to room temperature, 100 ml of water was added, and a precipitate was separated by filtration. The mother liquor was separated into the organic and aqueous layers, the aqueous layer was washed with 100 ml of toluene, and the organic layers were combined, concentrated, and dried under reduced pressure to give 17.9 g of a crude product. The crude product was treated with activated carbon, crystallized from THF/methanol, and purified by reslurrying under heat with ethyl acetate to give 11.7 g (0.017 mole, 69.7% yield) of 2,7-bis(N-3-biphenylyl-N-phenylamino)dibenzodioxin. The product showed a purity of 99.0 area % (HPLC, 254 nm). The product was purified further by sublimation; FD-MS, m/z 671 [M]+, m.p. 232° C., Tg 85° C.

Example 3

Synthesis of 2,7-bis(N-3-biphenylyl-N-3-pyridylamino)dibenzodioxin (Compound 3)

To a solution of 0.28 g (1.24 millimoles) of palladium (II) acetate in 20 ml of xylene was added 0.96 g (4.28 millimoles) of tri-tert-butylphosphine and the mixture was heated at 80° C. for 30 minutes with stirring. This solution was transferred into a solution heated at 80° C. of 9.0 g (0.024 mole) of 2,7-bis(3-pyridylamino)dibenzodioxin, 14.2 g (0.061 mole) of 3-bromobiphenyl, and 9.53 g (0.099 mole) of sodium tert-butoxide in 200 ml of xylene. The mixture was then heated up to 140° C. and heated at this temperature with stirring for 22 hours. The reaction mixture was cooled to room temperature, 200 ml of water was added, and a precipitate was separated by filtration. The mother liquor was separated into the organic and aqueous layers, the aqueous layer was washed with 200 ml of toluene, and the organic layers were combined, concentrated, and dried under reduced pressure to give 15.2 g of a crude product. The crude product was purified by silica gel column chromatography to give 5.25 g (0.0078 mole, 32.5% yield) of 2,7-bis(N-3-biphenylyl-N-3-pyridylamino)dibenzodioxin. The product showed a purity of 95.0 area % (HPLC, 254 nm). The product was purified further by sublimation; FD-MS, m/z 672 [M]+, melting point and glass transition temperature not observed.

Example 4

Synthesis of 2,7-bis(N-1-naphthyl-N-phenylamino)dibenzodioxin (Compound 8)

To a solution of 0.161 g (0.715 millimole) of palladium (II) acetate in 20 ml of xylene was added 0.58 g (2.86 millimoles) of tri-tert-butylphosphine and the mixture was heated at 80° C. for 30 minutes with stirring. This solution was transferred into a solution heated at 80° C. of 5.24 g (0.0143 mole) of 2,7-bis(phenylamino)dibenzodioxin, 7.41 g (0.0358 mole) of 1-bromonaphthalene, and 5.77 g (0.06 mole) of sodium tert-butoxide in 260 ml of xylene. The mixture was heated up to 135° C. and heated at this temperature with stirring for 4 hours. The reaction mixture was cooled to room temperature, and 200 ml of water was added. The organic layer was separated from the aqueous layer, the aqueous layer was washed with 200 ml of toluene, and the organic layers were combined, concentrated, and dried under reduced pressure to give 9.5 g of a crude product. The crude product was subjected to reslurrying under heat with ethyl acetate and dried under reduced pressure to give 3.40 g (0.0055 mole, 38.5% yield) of 2,7-bis(N-1-naphthyl-N-phenylamino)dibenzodioxin. The product showed a purity of 98.3 area % (HPLC, 254 nm). The product was purified further by sublimation; FD-MS, m/z 618 [M]+, m.p. 315° C., Tg 103° C.

Example 5

Synthesis of 2,7-bis(N-9-phenanthryl-N-phenylamino)dibenzodioxin (Compound 9)

To a solution of 0.12 g (0.55 millimole) of palladium (II) acetate in 10 ml of xylene was added 0.445 g (2.26 millimoles) of tri-tert-butylphosphine and the mixture was heated at 80° C. for 30 minutes with stirring. This solution was transferred into a solution heated at 80° C. of 4.03 g (0.011 mole) of 2,7-bis(phenylamino)dibenzodioxin, 7.07 g (0.0275 mole) of 1-bromophenanthrene, and 4.44 g (0.0462 mole) of sodium tert-butoxide in 200 ml of xylene. The mixture was then heated up to 135° C. and heated at this temperature with stirring for 3 hours. The reaction mixture was cooled to room temperature, 150 ml of water was added, and a precipitate was removed by filtration. The mother liquor was separated into the organic layer and the aqueous layer, the aqueous layer was washed with 200 ml of toluene, and the organic layers were combined, concentrated, and dried under reduced pressure to give 13.0 g of a crude product. The crude product was treated with activated carbon and crystallized from ethyl acetate/hexane to give 3.85 g (0.00536 mole, 48.7% yield) of 2,7-bis(N-9-phenanthryl-N-phenylamino)dibenzodioxin. The product showed a purity of 98.6 area % (HPLC, 254 nm). The product was purified further by sublimation; FD-MS, m/z 718 [M]+, m.p. not observed, Tg 149° C.

Example 6

Synthesis of 2,7-bis(9-carbazolyl)thianthrene (Compound 27)

To a solution of 0.7 g (3.1 millimoles) of palladium (II) acetate in 40 ml of xylene was added 3 ml (12.4 millimoles) of tri-tert-butylphosphine and the mixture was heated at 80° C. for 30 minutes with stirring. This solution was transferred into a solution heated at 80° C. of 6.5 g (0.0264 mole) of 2,7-diaminothianthrene, 20.5 g (0.0657 mole) of 2,2'-dibromobiphenyl, and 22.0 g (0.229 mole) of sodium tert-butoxide in 380 ml of xylene. The mixture was then heated up to 125° C. and heated at this temperature with stirring for 5 hours. The reaction mixture was cooled to room temperature, and 200 ml of water was added. A precipitate was collected by filtration and washed with THF to give 5.18 g (0.0095 mole, 36% yield) of 2,7-bis(9-carbazolyl)thianthrene. The product showed a purity of 99.1 area % (HPLC, 254 nm). The product was purified further by sublimation; APCI-TOFMS, m/z 547 [M+H]+, m.p. 350° C., Tg 137° C.

Example 7

An organic EL device was fabricated as illustrated in FIG. 1 while omitting the hole-injecting layer and adding an electron-injecting layer. Applying the technique of vacuum deposition at $4.0 \times 10^{-4}$ Pa, the layers in thin film were stacked one upon another on the glass substrate coated with a 150 nm-thick ITO anode.

First, a 60 nm-thick layer of NPB was deposited on the ITO as the hole-transporting layer. Next, Compound 12 and Ir(ppy)3 were codeposited from different evaporation sources to a thickness of 25 nm as the light-emitting layer. The concentration of Ir(ppy)3 was 7.0%. Following this, a 50 nm-thick layer of Alq3 was deposited as the electron-transporting layer and thereafter a 0.5 nm-thick layer of lithium fluoride (LiF) was deposited as the electron-injecting layer. Finally, an aluminum electrode was deposited to a thickness of 170 nm on the electron-injecting layer.

The organic EL device thus obtained was connected to an outside power source and, on application of DC voltage, it showed the luminous properties shown in Table 5. The values of the brightness, voltage, and luminous efficiency in Table 5 are those determined at 10 mA/cm². The maximum wavelength of the spectrum of light emitted from the device was 517 nm and this indicates that Ir(ppy)3 emitted light.

Example 8

An organic EL device was fabricated as in Example 7 with the exception of using Compound 3 as the main component of the light-emitting layer. The luminous properties are shown in Table 5.

Example 9

An organic EL device was fabricated as in Example 7 with the exception of using Compound 1 in the hole-transporting layer and TAZ as the main component of the light-emitting layer. The luminous properties are shown in Table 5.

Example 10

An organic EL device was fabricated as in Example 7 with the exception of using Compound 27 as the main component of the light-emitting layer. The luminous properties are shown in Table 5.

Comparative Example 1

An organic EL device was fabricated as in Example 7 with the exception of using HMTPD in the hole-transporting layer and TAZ as the main component of the light-emitting layer. The luminous properties are shown in Table 5.

Comparative Example 2

An organic EL device was fabricated as in Example 7 with the exception of using TAZ as the main component of the light-emitting layer. The luminous properties are shown in Table 5.

TABLE 5

| | Brightness (cd/m²) | Voltage (V) | Luminous efficiency (lm/W) | Half-life of brightness (h) |
|---|---|---|---|---|
| Ex. 7 | 2400 | 9.2 | 8.2 | 1500 |
| Ex. 8 | 2150 | 10.5 | 6.4 | 1220 |
| Ex. 9 | 2100 | 11.5 | 5.7 | 800 |
| Ex. 10 | 2550 | 9.1 | 8.8 | 1300 |
| Comp. Ex. 1 | 2050 | 13.2 | 4.9 | — |
| Comp. Ex. 2 | 1270 | 9.5 | 4.2 | — |

Example 11

An organic EL device was fabricated as illustrated in FIG. 1 with omission of the electron-transporting layer and addition of an electron-injecting layer. A 25 nm-thick layer of CUPC was deposited on the ITO layer of the ITO-coated glass substrate at a degree of vacuum of $(7-9) \times 10^{-5}$ Pa and a 45 nm-thick layer of Compound 8 was deposited on the CuPc layer to form the hole-transporting layer. Then, a 60 nm-thick layer of Alq3 was deposited on the hole-transporting layer to form the light-emitting layer and, further, LiF and Al were respectively deposited to a thickness of 6 Å and 170 nm to form the electron-injecting layer and the cathode.

The organic EL device thus obtained was connected to an outside power source and, on application of DC voltage, it showed the luminous properties shown in Table 6. The device tested emitted green light with a peak wavelength of 500 nm and this confirms that only Alq3 emitted light.

Example 12

An electroluminescent device was fabricated as in Example 11 with the exception of using Compound 9 to form the hole-transporting layer. The luminous properties are shown in Table 6.

Comparative Example 3

An electroluminescent device was fabricated as in Example 11 with the exception of using NPB to form the hole-transporting layer. The luminous properties are shown in Table 6.

TABLE 6

| | Hole-transporting material | Current density (mA/cm²) @1000 cd/m² | Voltage (V) @1000 cd/m² | Luminous efficiency (lm/W) @1000 cd/m² |
|---|---|---|---|---|
| Ex. 11 | Compound 8 | 24 | 8.0 | 1.70 |
| Ex. 12 | Compound 9 | 28 | 8.4 | 1.45 |
| Comp. EX. 3 | NPB | 30 | 7.0 | 1.45 |

INDUSTRIAL APPLICABILITY

The heterocyclic compound of this invention shows high mobility of electrical charges (electrons and holes) and, when applied to an organic EL device, it enables the device to drive at low voltage. When used as a host material, electrons and holes move well-balanced to form a wide range of emission of light and attain high luminous efficiency. Furthermore, the said heterocyclic compound has a high triplet energy which is important in an electroluminescent device utilizing phosphorescence. Hence, when used as a host material or an electron-transporting material for a phosphorescent device, the energy of the triplet excited state of a phosphorescent dopant can be confined efficiently and phosphorescence can be obtained at high efficiency. In addition to these good electrical properties, the said heterocyclic compound is stable when formed into thin film. An organic EL device comprising the heterocyclic compound of this invention in its organic layer efficiently emits light of high brightness at low voltage and shows excellent durability and it is applicable to flat panel displays (for example, office computers and wall-hanging television sets), vehicle display devices, cellular phone displays, light sources utilizing the characteristics of planar light emitters (for example, light sources of copiers and backlight sources of liquid crystal displays and instruments), signboards, beacon lights, and the like.

What is claimed is:

1. A heterocyclic compound represented by the following general formula (I)

wherein $X_1$ and $X_2$ independently denote O or S, and m and n independently denote 1 or 2, and wherein the groups —$NAr_1Ar_2$ and —$NAr_3Ar_4$ independently denote N-carbazolyl, N-phenoxazinyl, N-phenothiazinyl, or N-β-carbolinyl, either unsubstituted or substituted with a lower alkyl group, a lower alkoxy group, an aryl group of 4 to 10 carbon atoms, or an aryloxy group of 4 to 10 carbon atoms.

2. The heterocyclic compound as described in claim 1 wherein the groups —$NAr_1Ar_2$ and —$NAr_3Ar_4$ in general formula (I) denote N-carbazolyl, either unsubstituted or substituted with a lower alkyl group, a lower alkoxy group, an aryl group of 4 to 10 carbon atoms, or an aryloxy group of 4 to 10 carbon atoms.

3. A heterocyclic compound represented by the following general formula (I)

(I)

wherein $X_1$ and $X_2$ independently denote O or S, and m and n independently denote 1 or 2, and wherein the groups $Ar_1$, $Ar_2$, $Ar_3$, and $Ar_4$ independently denote phenyl, naphthyl, phenanthryl, pyridyl, pyrazyl, pyrimidyl, imidazolyl, thienyl, or furyl, either unsubstituted or substituted with a lower alkyl group, a lower alkoxy group, an aryl group of 4 to 10 carbon atoms, or an aryloxy group of 4 to 10 carbon atoms.

4. The heterocyclic compound as described in claim 3, wherein the groups $Ar_1$, $Ar_2$, $Ar_3$, and $Ar_4$ in general formula (I) independently denote phenyl, pyridyl, pyrazyl, pyrimidyl, imidazolyl, thienyl, or furyl, either unsubstituted or substituted with a lower alkyl group, a lower alkoxy group, an aryl group of 4 to 10 carbon atoms, or an aryloxy group of 4 to 10 carbon atoms.

5. The heterocyclic compound as described in claim 1 or 3, wherein $X_1$ and $X_2$ is O.

6. The heterocyclic compound as described in claim 1 or 3, wherein $X_1$ and $X_2$ is S.

7. An organic electroluminescent device comprising an organic layer containing the heterocyclic compound described in claim 1 or 3.

8. The organic electroluminescent device as described in claim 7 wherein the organic layer containing the heterocyclic compound is at least one layer selected from the group consisting of a light-emitting layer, hole-transporting layer, and hole-injecting layer.

9. The organic electroluminescent device as described in claim 7 wherein the organic layer containing the heterocyclic compound further contains a phosphorescent dopant.

10. The organic electroluminescent device as described in claim 7 wherein the organic layer containing the heterocyclic compound is a hole-transporting layer.

\* \* \* \* \*